(12) United States Patent
Ohrlander et al.

(10) Patent No.: US 8,470,453 B2
(45) Date of Patent: *Jun. 25, 2013

(54) BIOCOMPATIBLE SUBSTRATES AND USES THEREOF

(75) Inventors: Mattias Ohrlander, Enskede (SE); Billy Sodervall, Markaryd (SE)

(73) Assignee: Bactiguard AB, Stockholm (SE)

(*) Notice: Subject to any disclaimer, the term of this patent is extended or adjusted under 35 U.S.C. 154(b) by 887 days.

This patent is subject to a terminal disclaimer.

(21) Appl. No.: 11/784,332

(22) Filed: Apr. 5, 2007

(65) Prior Publication Data
US 2007/0237945 A1 Oct. 11, 2007

Related U.S. Application Data

(60) Provisional application No. 60/790,307, filed on Apr. 7, 2006.

(51) Int. Cl.
| | |
|---|---|
| B32B 15/04 | (2006.01) |
| B32B 15/16 | (2006.01) |
| B32B 15/20 | (2006.01) |
| B05D 1/00 | (2006.01) |
| B05D 1/18 | (2006.01) |
| B05D 3/00 | (2006.01) |
| A61L 27/00 | (2006.01) |
| A61L 31/00 | (2006.01) |
| A61L 33/00 | (2006.01) |

(52) U.S. Cl.
USPC .......... 428/670; 428/626; 428/673; 428/457; 428/219; 428/340; 428/403; 428/357; 427/2.1; 427/2.12; 427/2.13; 427/402; 427/404; 427/436; 427/328; 623/66.1

(58) Field of Classification Search
USPC ............. 428/626, 624, 625, 673, 670, 674, 428/457, 687, 220, 219, 332, 336, 669, 671, 428/672, 215, 216, 328, 323, 340, 402, 403, 428/357, 426, 936, 537.1, 408
See application file for complete search history.

(56) References Cited

U.S. PATENT DOCUMENTS

| | | | | |
|---|---|---|---|---|
| 4,795,475 | A * | 1/1989 | Walker | 128/898 |
| 5,320,908 | A * | 6/1994 | Sodervall et al. | 428/461 |
| 5,395,651 | A | 3/1995 | Sodervall et al. | |
| 5,695,857 | A | 12/1997 | Burrell et al. | |
| 5,747,178 | A | 5/1998 | Sodervall et al. | |
| 5,753,251 | A | 5/1998 | Burrell et al. | |
| 5,935,719 | A | 8/1999 | Abbott | |
| 5,965,204 | A | 10/1999 | Sodervall et al. | |
| 6,080,490 | A | 6/2000 | Burrell et al. | |
| 6,168,633 | B1 | 1/2001 | Shoher et al. | |
| 6,224,983 | B1 | 5/2001 | Sodervall et al. | |
| 6,284,387 | B1 * | 9/2001 | Nakao | 428/457 |
| 6,399,039 | B2 | 6/2002 | Ostgard | |
| 6,716,895 | B1 | 4/2004 | Terry | |
| 6,831,024 | B2 | 12/2004 | Kim | |
| 7,195,615 | B2 | 3/2007 | Tan | |
| 2004/0121077 | A1 | 6/2004 | Park et al. | |
| 2005/0159306 | A1 | 7/2005 | Kezuka et al. | |
| 2006/0003019 | A1 | 1/2006 | Møller et al. | |
| 2006/0251874 | A1 | 11/2006 | McClure et al. | |
| 2007/0237946 | A1 | 10/2007 | Ohrlander et al. | |

FOREIGN PATENT DOCUMENTS

| | | |
|---|---|---|
| CA | 2016081 C | 4/1999 |
| CH | 654738 | 3/1986 |
| EP | 0400349 A1 | 12/1990 |
| EP | 0693576 A1 | 1/1996 |
| EP | 0937398 A1 | 8/1999 |
| EP | 1375700 A1 | 1/2004 |
| JP | 63-200752 A | 8/1988 |
| JP | 11302570 | 2/1999 |
| JP | 2001234392 | 8/2001 |
| WO | 02/17984 A1 | 3/2002 |
| WO | WO-03063925 A1 | 8/2003 |
| WO | WO-03076341 A2 | 9/2003 |
| WO | WO-2004/045577 A1 | 6/2004 |
| WO | 2005/072281 A2 | 8/2005 |
| WO | WO-2005073289 | 8/2005 |
| WO | 2005/072281 A3 | 11/2005 |

OTHER PUBLICATIONS

Møller, Per et al. (2007). "A New Approach for Biologically-Inhibiting Surfaces," *Journal of Applied Surface Finishing* 2(2): 149-157.
International Search Report mailed Jul. 4, 2007, for PCT Application No. PCT/SE2007/050226 filed Apr. 5, 2007, 6 pages.
International Search Report mailed Jul. 4, 2007, for PCT Application No. PCT/SE2007/050225 filed Apr. 5, 2007, 6 pages.
U.S. Appl. No. 12/296,429, filed Apr. 5, 2007 for Ohrlander at al.
Gabriel, M. M. et al. (1995). "Effects of Silver on Adherence of Bacteria to Urinary Catheters: In Vitro Studies," *Current Microbiology* 30:17-22.
U.S. Appl. No. 07/347,016, filed May 4, 1989 for Sodervall et al.
U.S. Appl. No. 07/630,333, filed Dec. 13, 1990 for Sodervall et al.
Saygan, O. et al. (2006). "Gold and Gold-Palladium Coated Polypropylene Graft in a *S epidermidis* Wound Infection Model," *Journal of Surgical Research* 131:73-79.
International Search Report mailed Mar. 1, 2007, for PCT Application No. PCT/SE2006/050485 filed Nov. 16, 2006, five pages.
Non Final Office Action received for U.S. Appl. No. 11/784,558, mailed on Mar. 24, 2010, 18 pages.
Final Office Action received for U.S. Appl. No. 11/784,558, mailed on Dec. 8, 2010, 17 Pages.

(Continued)

*Primary Examiner* — Michael La Villa
(74) *Attorney, Agent, or Firm* — Morrison & Foerster LLP

(57) ABSTRACT

A new substrate makes it possible to modify surface properties relating to biocompatibility. Said substrate has an electron donating surface, characterized in having metal particles on said surface, said metal particles comprising palladium and at least one metal chosen from gold, ruthenium, rhodium, osmium, iridium, and platinum, wherein the amount of said metal particles is from about 0.001 to about 8 $\mu g/cm^2$. The substrate is suggested for different uses, such as for modifying the hydrophobicity, protein adsorption; tissue ingrowth, complement activation, inflammatory response, thrombogenicity, friction coefficient, and surface hardness.

30 Claims, No Drawings

OTHER PUBLICATIONS

Non Final Office Action received for U.S. Appl. No. 12/296,429, mailed on Jul. 12, 2011, 25 pages.

Final Office Action received for U.S. Appl. No. 12/296,429, mailed on Mar. 9, 2012, 15 pages.

Extended European Search Report received for European Patent Application No. 07748386.5, mailed on Aug. 2, 2012, 5 pages.

Non Final Office Action Received for U.S. Appl. No. 13/155,334, mailed on May 22, 2012, 33 pages.

Notice of Allowance received for U.S. Appl. No. 12/296,429, mailed on Jul. 5, 2012, 12 pages.

Notice of Allowance received for U.S. Appl. No. 13/155,334, mailed on Nov. 26, 2012, 10 pages.

* cited by examiner

BIOCOMPATIBLE SUBSTRATES AND USES THEREOF

RELATED APPLICATION

This application claims priority to U.S. Provisional Application Ser. No. 60/790,307 filed Apr. 7, 2006, which is hereby incorporated by reference in its entirety.

FIELD OF THE INVENTION

The present invention relates to a new substrate with nano particles, which makes it possible to modify surface properties relating to biocompatibility in a repeatable and controlled manner. Examples of surface properties, which can be modified, include but are not limited to hydrophobicity, protein adsorption, tissue ingrowth, complement activation, inflammatory response, thrombogenicity, friction coefficient, and surface hardness. The present invention further relates to objects comprising said new substrate. The present invention further relates to the use of said substrate. Finally the present invention further relates to a method for the manufacture of such a substrate.

BACKGROUND

It has always been desirable to modify surface characteristics to achieve useful properties. In particular it is desired to be able to modify surface properties that are important in connection with biocompatible objects.

SHORT SUMMARY OF THE PRESENT INVENTION

A problem in the state of the art regarding surfaces is how to provide a surface which is biocompatible, wherein it in a repeatable way is possible to modify the hydrophobicity, protein adsorption, tissue ingrowth, complement activation, inflammatory response, thrombogenicity, friction coefficient, and surface hardness.

The present inventors have discovered that the above-mentioned problem in the state of the art is solved by a substrate having an electron donating surface, characterized in that there are metal particles on the surface. The metal particles include palladium and at least one metal chosen from gold, ruthenium, rhodium, osmium, iridium, and platinum and wherein the amount of said metal particles is from about 0.001 to about 8 µg/cm². Further embodiments of the present invention are defined in the appended dependent claims.

DESCRIPTION

Definitions

Before the invention is disclosed and described in detail, it is to be understood that this invention is not limited to particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

The following terms are used throughout the description and the claims.

"Biocompatible" as used herein is the ability of a material to perform with an appropriate host response in a specific application.

"Biofilm" as used herein is a thin layer in which microorganisms are embedded. Biofilms occur when microorganisms colonise a surface.

"Complement activation" as used herein is a complex system of factors in blood plasma that may be activated by a chain reaction from component C1 to C9, which give rise to a number of biological effects. Complement activation occurs in two ways a) the classical C1 to C9, or b) the alternative by direct activation of C3.

"Contact angle". For a given droplet on a solid surface the contact angle is a measurement of the angle formed between the surface of a solid and the line tangent to the droplet radius from the point of contact with the solid.

"Electron donating material" as used herein is a material, which in connection with another more noble material has the ability to transfer electrons to the more noble material. An example is a less noble metal together with a more noble metal.

"Electron donating surface" as used herein is a surface layer comprising an electron donating material.

"Hydrophobicity" of a surface as used herein describes the interactions between the surface and water. Hydrophobic surfaces have little or no tendency to adsorb water and water tends to "bead" on their surfaces. The term hydrophobicity of a surface is also closely linked with its surface energy. Whereas surface energy describes interactions of the surface with all molecules, the hydrophobicity describes the interactions of the surface with water.

"Hysteresis of contact angle" as used herein is the difference between the advancing and receding contact angle values. The advancing contact angle of a drop of water on a surface is the contact angle when the boundary between water and air is moving over and wetting the surface, while the receding angle is the contact angle when boundary between water and air is withdrawn over a pre-wetted surface.

"Inflammatory response" occurs when tissues are injured by viruses, bacteria, trauma, chemicals, heat, cold or any other harmful stimulus. Chemicals including bradykinin, histamine, serotonin and others are released by specialised cells. These chemicals attract tissue macrophages and white blood cells to localise in an area to engulf and destroy foreign substances.

"Modify" either means reducing or enhancing a property.

"Noble" is used herein in a relative sense. It is used to relate materials including metals to each other depending on how they interact with each other. When two metals are submerged in an electrolyte, while electrically connected, the term "less noble" metal is used to denote the metal which experiences galvanic corrosion. The term "more noble" is used to denote the other metal. Electrons will be transferred from the "less noble" metal to the more noble metal.

"Protein adsorption" as used herein is the phenomenon where proteins adhere to a surface due to overall attractive forces between the proteins and the surface.

"Substrate" as used herein is the base, which is treated according to the present invention.

"Tissue ingrowth" is the process where cells start to grow on a surface, forming new tissue.

"Thrombogenicity" as used herein is the ability of a substrate to induce clotting of blood.

DETAILED DESCRIPTION OF THE PRESENT INVENTION

According to the present invention a substrate is treated to give it desired properties. The substrate can be made of a wide range of materials. In one embodiment the substrate is made of a material, which has an electron-donating surface. In the case of an electron-donating surface the metal particles can be applied directly on to the electron-donating surface. In the case where the surface it not electron donating, a layer of an electron donating material has to be applied to create an electron donating surface.

The present disclosure describes a substrate having an electron donating surface. The substrate includes metal particles. The metal particles include palladium and at least one metal chosen from gold, ruthenium, rhodium, osmium, iridium, and platinum. The amount of metal particles is from about 0.001 to about 8 $\mu g/cm^2$ on the surface. A preferred amount of the metal particles is from about 0.01 to about 4 $\mu g/cm^2$. A particularly preferred amount of the metal particles is from about 0.01 to about 1 $\mu g/cm^2$.

Either the substrate itself is electron donating or there is applied a layer of an electron donating material on the substrate. In the case where the electron donating material is applied on the substrate it is applied in an amount of from about 0.05 to about 12 $\mu g/cm^2$.

An electron donating material does not necessarily have an electron-donating surface. An example is aluminium, which in air gets an oxide layer, which is not an electron-donating surface.

The electron donating material is any material with the ability to form an electron-donating surface, such as a conducting polymer or a metal. In the case of a metal it must be less noble than any of the metals in the group consisting of palladium, gold, ruthenium, rhodium, osmium, iridium, and platinum.

A preferred metal for use as an electron-donating surface is a metal chosen from silver, copper and zinc.

In one embodiment of the present invention the substrate is a polymeric substrate.

In one embodiment the substrate is chosen from latex, vinyl, polymers comprising vinyl groups, polyurethane urea, silicone, polyvinylchloride, polypropylene, styrene, polyurethane, polyester, copolymerisates of ethylene vinyl acetate, polystyrene, polycarbonate, polyethylene, polyacrylate, polymethacrylate, acrylonitrile butadiene styrene, polyamide, and polyimide, or mixtures thereof. In another embodiment of the present invention the substrate is chosen from a natural polymer, a degradable polymer, an edible polymer, a biodegradable polymer, an environmental friendly polymer, and a medical grade polymer.

In another embodiment of the present invention the substrate is a metal.

A preferred metal for the substrate is chosen from stainless steel, medical grade steel, titanium, medical grade titanium, cobalt, chromium and aluminium or mixtures thereof.

In another embodiment of the present invention the substrate is chosen from glass, minerals, zeolites, stone and ceramics.

In another embodiment of the present invention the substrate is chosen from paper, wood, woven fibres, fibres, cellulose fibres, leather, carbon, carbon fibres, graphite, polytetrafluoroethylene, and polyparapheneneterephthalamide.

In another embodiment of the present invention the substrate has the shape of a particle. In this embodiment particles are coated according to the present invention. Such particles can have a spherical shape or an irregular shape.

In one embodiment of the present invention there is provided an object comprising a substrate according to the present invention. Examples of an object comprising a substrate according to the present invention are medical devices, medical instruments, disposable articles, medical disposable articles.

The particles must always include palladium. In addition to palladium there is at least one other metal. A ratio of palladium to other metals in the metal particles of from about 0.01:99.99 to about 99.99:0.01 can be used in the present invention. A ratio from about 0.5:99.5 to about 99.8:0.2 is preferred. Particularly preferred ratios are from about 2:98 to about 95:5. Very particularly preferred ratios are 5:95 to 95:5. In another embodiment the ratios are from about 10:90 to about 90:10.

In one embodiment of the present invention the metal particles, in addition to palladium, include gold.

The present inventors have discovered that advantageous properties are achieved when the metal particles have an average size of from about 10 to about 10000 Å.

In one embodiment the average sizes for the metal particles are from about 100 to about 600 Å.

In another aspect of the present invention there is provided an object comprising any of the substrates described herein.

There is also provided a medical device comprising any of the substrates described herein.

A disposable article comprising any of the substrates described herein is also provided.

The present invention also provides a dental article, as well as dental equipment, dental implants, and dental devices, including any of the substrates described herein.

The applied amount of the metal particles is expressed as a surface concentration in $\mu g/cm^2$ and it must be realised that the metal particles do not form a covering layer, but instead are uniformly distributed particles or clusters on said electron donating surface. Thus this is a measure of the weight of the particles on an area of the substrate.

An applied layer of an electron donating material is preferably applied so that it is uniform, essentially without agglomerates or clusters on the surface. If the electron donating surface layer is homogenous and uniform the applied amount in $\mu g/cm^2$ may be converted to a thickness in Å. An applied amount of 0.05-4 $\mu g/cm^2$ corresponds to about 4.8-380 Å, 0.5-8 $\mu g/cm^2$ corresponds to about 48-760 Å, and 0.8-12 $\mu g/cm^2$ corresponds to about 76-1140 Å.

In one embodiment of the present invention the electron-donating surface is a layer of commercially available essentially pure silver, which does not exclude the possibility of small amounts of impurities.

If the substrate does not have an electron donating surface and thus a deposition of an electron donating surface layer is necessary, the deposition is performed using a method chosen from chemical vapour deposition, sputtering, and deposition of metal from a solution comprising a metal salt. A uniform layer essentially without clusters or agglomerates is the result of the deposition. Preferably the deposition is carried out so that the first layer has good adhesion to the substrate.

Now there is described one embodiment of the present invention for preparation of the coated substrate. For substrates which do not have an electron donating surface the method include some or all of the following steps:
1. pre-treatment
2. rinsing
3. activation
4. deposition of an electron donating surface
5. rinsing
6. deposition of metal particles 7. rinsing
8. drying For objects with an electron-donating surface the method comprises the steps
1. rinsing
2. deposition of metal particles
3. rinsing
4. drying In the following, one embodiment of steps 1 to 9 for substrates which do not have an electron-donating surface is described more in detail.

The pre-treatment can be made in an aqueous solution of a stannous salt containing from about 0.0005 to about 30 g/l of stannous ions. The pH is from about 1 to about 4 and adjusted by hydrochloric and/or sulphuric acid. The treatment time is from about 2 to about 60 minutes at room temperature. After the pre-treatment the surface is rinsed in demineralised water, but not dried.

The activated and rinsed substrate is transferred to the deposition solution. The deposition solution has a pH of not less than about 8. It includes a metal salt chosen from a silver salt, a zinc salt, and a copper salt. In one embodiment of the present invention the salt is silver nitrate ($AgNO_3$). The metal salt is used in an effective amount of no more than about 0.10 grams per liter, preferably about 0.015 grams per liter. If the metal content is above about 0.10 grams per liter, the elemental metal may form nonuniformly, in the solution or on the container walls. If the metal content is below an effective amount, there is insufficient metal to form a film in the desired time.

A second component of the deposition solution is a reduction agent that reduces the metal-containing salt to elemental metal. The reduction agent must be present in an amount sufficient to accomplish the chemical reduction. Acceptable reduction agents include formaldehyde, hydrazine sulphate, hydrazine hydroxide, and hypo phosphoric acid. In one embodiment of the present invention it is present in an amount of about 0.001 milliliters per liter of solution. Too large a concentration of the reduction agent causes deposition of metal throughout the solution and on the container walls, while too small a concentration may result in an insufficient formation of metal on the substrate. A person skilled in the art can in the light of this description by routine experimentation determine the desired amount of reduction agent.

Another component of the deposition solution is a deposition control agent that is present in an amount sufficient to slow the deposition reaction to prevent the reduced metal from precipitating directly from solution as a fine metallic powder, or precipitating onto the walls of the container. Operable deposition control agents include inverted sugar, also known as invertose, succinic acid, sodium citrate, sodium acetate, sodium hydroxide, potassium hydroxide, sodium tartrate, potassium tartrate, and ammonia. The deposition control agent is preferably present in an amount of about 0.05 grams per liter of solution. If too little is present, there may occur precipitation of metal clusters instead of a uniform metallic surface. If too much is present, the metal-containing salt may become too stable for the desired precipitation onto the substrate of interest.

The concentrations of the reduction agent and the deposition control agent are adjusted as necessary to achieve the desired results, depending upon the substrate material, the thickness of the film desired, the conditions of deposition, and the concentration of metal in the solution. For example, for thin films the metal salt concentration will be relatively low, as will the concentrations of the reduction agent and the deposition control agent. A person skilled in the art can in the light of this description by routine experimentation determine the desired amount of deposition control agent.

In preparing the deposition solution, each of the components of the solution are preferably individually dissolved in demineralised water. The various pre-solutions are then mixed, and diluted where necessary, in the correct amounts to achieve the concentrations mentioned above.

The combination of a metal salt and reduction agent permits the metal to be reduced from the salt in a suitable state to be deposited upon the surface of the substrate. This method is particularly beneficial to achieve good adhesion of the completed metal film to the substrate surface. Good adhesion is important in nearly all uses.

The substrate surface is exposed to the deposition solution by any appropriate procedure. Dipping into the solution is normally preferred, but the solution may be applied by any convenient technique such as spraying or brushing. The metal film deposits uniformly from the solution at a rate that may be controlled by the concentration of the metal salt. If a thin film is required, the temperature of deposition is maintained sufficiently low so that deposition is controllably slow.

Other methods of applying a metal layer that acts as an electron-donating surface can also be applied in the present invention. Other ways of achieving an electron-donating surface are chemical vapour deposition and sputtering.

After the above-described metal deposition the substrate has an electron-donating surface consisting of a metal. This metal deposition is only necessary if the substrate does not have an electron-donating surface from the start. If the substrate already possesses an electron-donating surface, metal particles can be deposited on the surface without the extra addition of a metal layer. In the latter case the substrate is cleaned thoroughly before application of the particles.

The next step in the manufacturing method is deposition of metal particles.

In one embodiment colloidal suspensions of metals are used to obtain particles comprising palladium and at least another metal on the surface. The metal particles are deposited from a suspension of the desired particles. The composition of the metal particles in the suspension is adjusted according to the preferred value. The substrate with the electron-donating surface is dipped in the suspension of metal particles for a period of time from about a few seconds to about a few minutes or longer.

The suspension of metal particles can be manufactured in several ways. In one embodiment the suspension of metal particles is made from an aqueous solution of a metal salt which is reduced under conditions such that metal particles of a desired size are formed. Mixing a suitable amount of metal salt, reducing agent and stabilising agent achieves this. The same reducing agents and stabilising agents as described above can be used when making the particle suspension. A person skilled in the art can in the light of this description by routine experimentation determine the desired amount of reducing agent and stabilising agent to get the desired particle size. In an alternative embodiment a commercially available colloidal suspension of metal particles is used. Metal particles of the desired composition are used to make the suspension.

In one embodiment the suspension of metal particles is made by diluting with demineralised water a commercially available concentrated colloidal solution of metal particles comprising palladium and at least one metal chosen from gold, ruthenium, rhodium, osmium, iridium, and platinum. The substrate is treated with the suspension for a period of time from about a few seconds to about a few minutes or longer. After the treatment the substrate is rinsed in a solvent or water such as demineralised water and left to dry in room temperature.

In one particular non-limiting embodiment the commercially available metal particles consist of 75% palladium and 25% gold.

Thus according to the present invention, a substrate with a particular desired surface can be obtained. For example, one can prepare a substrate having a silver electron donating surface with particles consisting of 75% palladium and 25% gold, or a copper electron donating surface with particles consisting of 85% palladium and 15% ruthenium.

One of the advantages offered by the flexible yet controlled and repeatable method for producing such substrates is that a wide variety of substrates can be produced. As described further herein, certain substrates have improved properties over existing substrates. For example a particular substrate according to the present invention can produce surprising and advantageous modifications of the hydrophobicity of a substrate to which is it applied. Other properties that can be modified in this way by substrates according to claim 1 include protein adsorption, tissue ingrowth, complement activation, inflammatory response, thrombogenicity, friction coefficient, and surface hardness.

That is, it is possible to adjust the particle size, the composition of the particles and the amount of particles to modify the surface properties of objects to which the substrate is applied.

The present inventors have discovered that it is possible to achieve this by using a substrate according to claim 1. In particular it is possible to adjust the particle size, the composition of particles, and the amount of particles to modify the surface properties.

Substrates according to the present invention can be used for many purposes. They are suitable for use in any application where it is desired to modify hydrophobicity, protein adsorption, tissue ingrowth, complement activation, inflammatory response, thrombogenicity, friction coefficient, and surface hardness of a substrate.

Properties of the substrate can be both reduced or increased. Thus objects are provided which display at least one area which enhances a feature, and at least one area which reduces a feature. An example is an object with an area that reduces protein adsorption and an area that enhances protein adsorption. Another example is an object with an area that reduces tissue ingrowth and an area that enhances tissue ingrowth.

A substrate according to the present invention also comprises a substrate having an electron donating surface, with metal particles on said surface, said metal particles comprise palladium wherein the amount of said metal particles is from about 0.001 to about 8 $\mu g/cm^2$.

The present invention provides use of a substrate according to the present invention for modifying the protein adsorption to an object comprising said substrate.

The present invention provides use of a substrate according to the present invention for modifying the tissue ingrowth on an object comprising said substrate.

The present invention provides use of a substrate according to the present invention for modifying the complement activation caused by an object comprising said substrate.

The present invention provides use of a substrate according to the present invention for modifying the inflammatory response caused by an object comprising said substrate.

The present invention provides use of a substrate according to the present invention for modifying the blood clotting caused by an object comprising said substrate.

Another advantage of the substrate according to the appended claims is that it provides a possibility to modify the friction coefficient and surface hardness. Thus there is provided the use of a substrate according to the present invention for the modification of the friction coefficient of an object comprising said substrate.

Other features of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Hydrophobicity of the Surface as a Function of the Amount of Metal Particles

A uniform layer of silver was deposited on a glass substrate according to the following method. The substrate was immersed in a cleaning solution of chromic acid for 5 minutes at 58° C., followed by rinsing in demineralised water. The surface of the substrate was activated by immersion in a solution of aqueous stannous chloride and then rinsed in demineralised water. The surface of the substrate was then plated with a uniform layer of silver by immersion in 3 deposition solutions comprising silver ions. This yielded a silver surface with an applied amount of 1.2 $\mu g/cm^2$ corresponding to a thickness of about 115 Å. Particles consisting of 23% palladium and 77% gold were subsequently deposited on the first silver surface by immersion in a dilute suspension comprising metal particles of gold/palladium. The suspension of metal particles was made by reducing a gold salt and a palladium salt with a reducing agent and stabilising the suspension with a stabilising agent. The substrate was subsequently rinsed in demineralised water and dried.

Substrates with different amounts of deposited particles were made using the method outlined above. Amounts of particles were 0, 0.02, 0.11, 0.15, and 0.19 $\mu g/cm^2$ respectively. For the sample with 0 $\mu g/cm^2$ no particles were deposited on the surface and hence it consists of a silver surface.

The static contact angle of a drop of water in equilibrium on the different substrates was measured. The advancing and receding contact angles were measured using the Wilhelmy technique.

The difference between the advancing and receding contact angle values is called the contact angle hysteresis and was calculated for the measurements. The result of the experiment is depicted in Table 1.

TABLE 1

| Amount of particles ($\mu g/cm^2$) | Static contact angle (degrees) | Contact angle hysteresis (degrees) |
|---|---|---|
| 0 | 52 | 70 |
| 0.02 | 50 | 77 |
| 0.11 | 56 | 75 |
| 0.15 | 62 | 80 |
| 0.19 | 62 | 84 |

The surface hydrophobicity of the substrate is thus modified while the surface displays several other useful properties, such as biocompatibility, inherent of the substrates according to this example.

Example 2

Protein Adsorption as a Function of the Amount of Metal Particles

A uniform layer of silver was deposited on a silicon dioxide substrate. The substrate was immersed in a cleaning solution of 20% sulphuric acid for 10 minutes at room temperature, followed by rinsing in demineralised water. The surface of the substrate was activated by immersion in an aqueous solution of stannous chloride and the rinsed in demineralised water. The surface of the substrate was then plated with a uniform layer of silver by immersion in 4 baths of deposition solutions comprising silver ions. This yielded a silver surface with an applied amount of 0.8 µg/cm$^2$ corresponding to a thickness of about 77 Å. Particles consisting of 95% palladium and 5% gold were subsequently deposited on the first silver surface by immersion in a dilute suspension of Pd/Au-particles. The applied amount of metal particles was 0.05, 0.12, 0.48 and 0.59 µg/cm$^2$ respectively. The substrate was rinsed in demineralised water and dried.

Adsorption of fibrinogen was studied by the QCM-D technique. Fibrinogen is a glycoprotein synthesised in the liver and is found in blood plasma. QCM-D is a quartz crystal microbalance with dissipation monitoring.

The adsorbed amount of fibrinogen as a function of applied metal particles is shown in table 2.

TABLE 2

| Amount of Pd/Au-particles (µg/cm$^2$) | Fibrinogen adsorption (µg/cm$^2$) |
|---|---|
| 0.05 | 2.5 |
| 0.12 | 2.8 |
| 0.48 | 1.8 |
| 0.59 | 2.3 |

Example 3

A net of polyester fabric was first rinsed in a 5% potassium hydroxide solution for 5 min at 30° C. After repeated rinsing in demineralised water the substrate was immersed in an acidified solution of 1 g/l stannous chloride at room temperature for 10 min. After rinsing in demineralised water it was soaked in a plating bath containing 2 g/l copper sulphate, 5 g/l sodium hydroxide, 50 g/l sodium citrate and 0.005 ml/l formaldehyde for 10 min at 35° C. A copper layer of about 200 Å was obtained and after new rinsing in demineralised water the substrate was immersed in a particle suspension comprising 0.05 g/l each of palladium particles and gold particles. The applied amount of metal particles was 0.4 µg/cm$^2$.

Example 4

A substrate of PMMA was cleaned in 5% hydrochloric acid for 2 min and then rinsed in demineralised water before dipping in a solution containing 0.02 g/l of the stannous ion at a pH of 2.5. After rinsing the substrate was immersed in a solution containing 0.005 g/l of silver ions, 0.02 ml/l ammonia, 0.05 g/l potassium hydroxide and 0.0005 ml/l formaldehyde for 5 min at room temperature. This gave a surface with 0.12 µg/cm$^2$ of silver. After rinsing it was immersed in a particle suspension comprising 0.005 g/l palladium and 0.002 g/l gold particles. The applied amount of metal particles was 0.05 µg/cm$^2$

Example 5

A non-woven polyimide substrate was immersed in a 12% solution of NaOH at 40° C. for 10 min. After repeated rinsing in demineralised water it was immersed in an alcoholic solution containing 0.5 g/l stannous chloride for 5 min at room temperature. After rinsing it was soaked in a copper bath according to example 3. A copper layer of 2 µg/cm$^2$ was obtained. After rinsing it was immersed in a suspension comprising 1% of Pd and 0.2% of gold particles, calculated on the weight of the total suspension. The applied amount of metal particles was 0.6 µg/cm$^2$.

Example 6

A nylon fabric was cleaned in 5% NaOH for 10 min at 40° C. and after rinsing in demineralised water immersed in a solution of 0.6 g/l stannous chloride at pH 2.2 for 15 min at room temperature. After this the surface comprised a silver amount of 0.8 µg/cm$^2$. After a new rinsing it was dipped in a silver bath according to example 2 and then after new rinsing dipped in a suspension comprising 1% Pd and 0.05% Au particles. The applied amount of metal particles was 0.12 µg/cm$^2$.

Example 7

A substrate of aluminium was treated in a solution of 10% nitric acid and 3% hydrofluoric acid at 60° C. for 20 min. After rinsing, the substrate was dipped in an acidified solution of 3 g/l stannous chloride and after renewed rinsing in a silver bath according to example 2. After this step an amount of around 80 Å silver was obtained on the surface. After another rinsing the substrate was immersed in a suspension comprising 1% Pd and 2% Au particles. The applied amount of metal particles was 0.7 µg/cm$^2$.

Example 8

A substrate of PTFE was etched in an aqueous solution of sodium hydroxide for 5 min. After rinsing and drying it was immersed in a solution containing 0.7 g/l stannous chloride for 20 min at room temperature. The substrate was after rinsing dipped in a plating bath containing 0.2 g/l silver nitrate, 0.5 ml/l ammonia and sodium hydroxide to pH 10.5 for 5 min. After this step an amount of around 2.2 µg/cm silver was obtained on the surface. After a new rinse it was immersed in a suspension comprising 3% Pd and 0.1% Au particles for 5 min at room temperature. The applied amount of metal particles was 0.03 µg/cm$^2$.

Example 9

A glass plate was rinsed in 10% sulphuric acid and 1% hydrofluoric acid at room temperature for 15 min. After rinsing it was immersed in a 1% stannous fluoride solution and after a new rinse immersed in a silver bath according to example 2. After this step an amount of around 140 Å silver was obtained on the surface. After renewed rinsing it was dipped in a suspension comprising 1% ruthenium and 2% palladium particles. The applied amount of metal particles was 0.25 µg/cm$^2$.

Example 10

A stainless steel substrate was immersed in a solution of 15% nitric acid and 5% HF at room temperature for 30 min and then rinsed in demineralised water. The process continued following the steps in example 11. The applied amount of metal particles was 0.9 µg/cm$^2$.

Example 11

A titanium rod was cleaned in a solution of 18% nitric acid and 2% HF for 20 min at room temperature. The application of an electron donating surface and the application of metal particles was made as in example 11. The applied amount of metal particles was 0.6 µg/cm$^2$.

Example 12

Detection of Surface Induced Complement Activation with Quartz Crystal Microbalance with Dissipation Monitoring (QCM-D)

The quantification of a foreign body response is indirectly achieved by monitoring the binding of rabbit-anti human antibodies directed to the surface bound complement factor C3b.

Within seconds from introduction to a soft tissue a foreign body is subject to great attention from the complement system. The complement system comprises about 30 different proteins where C3 is the most abundant. After high concentration body fluid proteins (i.e. Albumin, Fibrinogen and Fibronectin) the complement system is one of the first actors on the scene and aims to protect the host from invading bacteria and fungi, but also to alert the immune system about a foreign body entering the system.

Without being bound by any specific scientific theory the inventors assume that when complement factor 3 (C3) binds to an introduced surface it is cleaved by C3 convertase to form soluble C3a, and surface bound C3b. The surface bound C3b will then act as a convertase itself, triggering subsequent cleavage of C3 in a cascade-like fashion. Receptors to C3b is found on erythrocytes, macrophages, monocytes, polymorphonuclear leukocytes and B cells, all of which are important in controlling inflammation and wound healing in tissue. The exact mechanisms controlling the binding of C3 to the surface are still much unknown. However, antibodies directed specifically towards C3b can easily be measured in vitro with QCM-D and give quantitative information of a biomaterial's immune response properties. This new methodology show good agreement with all other known methods for the detection of surface bound C3b.

Material and Methods
Preparation of Surfaces

As model surfaces standard QCM-D crystals sputtered with Au (s), Ti (s) (QSX301 and QSX310 respectively) was used. A coating according to the present invention was applied on standard SiO$_2$ QCM-D crystals (QSX 303, Q-Sense Sweden) using the method outlined in example 2.

Blood Products

We received fresh whole blood from five healthy donors (Sahlgrenska University Hospital, Göteborg, Sweden). The blood was left to clot in room temperature for approximately 4 hours to obtain complement active serum. The serum was then centrifuged at 4000 rpm for 20 min (Hettich Universal 16 R) after which the supernatant was removed and re-centrifuged as above and stored at −70° C.

For detection of surface induced complement activation the serum was diluted 1:5 in Veronal Buffer Saline supplemented with CaCl$_2$ (0.15 mM) and MgCl$_2$ (0.5 mM) (VBS$^{++}$), and the adsorption of serum proteins to the modified QCM-D-crystals were monitored for 20 minutes followed by a rinse with buffer for 5 minutes. The rinse was followed by the addition of rabbit-anti-human C3b antibodies diluted 1:20 in VBS$^{++}$ (Sigma). For negative and positive controls, standard gold QCM-D crystals pre-coated with human IgG (1 mg/ml) (Sigma) were used. The negative control was heat inactivated at 56° C. for 30 min prior to measurements.

All experiments were carried out at room temperature in Veronal Buffer Saline with CaCl$_2$ (0.15 mM) and MgCl$_2$ (0.5 mM) (VBS$^{++}$) except for negative controls were VBS$^{--}$ were used. All QCM-D measurements were preformed on the apparatus D300 (Q-sense, Sweden).

Results

The SiO$_2$ surfaces coated as described above had an amount of silver of 0.35-0.61 µg/cm$^2$. The amount of gold in the particles was varied according to the table below and the complement activation was measured according to the table.

| Sample | Amount of Au (µg/cm$^2$) | C3b (ng/cm$^2$) |
|---|---|---|
| Sample No 1 | 0.09 | 677 |
| Sample No 2 | 0.41 | 991 |
| Neg control | — | 109 |
| Pos control | — | 1832 |
| Titan (control) | — | 632 |

Example 13

Platelet Adhesion and Soluble Complement Factor C3a Production on Biomaterial Surfaces The consumption of platelets in fresh whole blood exposed to a biomaterial is used to quantify the thrombogenicity of a desired biomaterial. Moreover, the soluble fraction of activated complement factor 3 (C3a) is used to monitor the complement activation from the biomaterial surface.

Background

Platelets (or thrombocytes) are small disc-shaped anuclear cell fragments normally present in healthy blood. They play a crucial role in preserving the walls in blood vessels and are recruited to a damaged area and activated to form a plug, preventing hemorrhage and blood loss. Platelets are also known to adhere and become activated on certain biomaterial surfaces, sometimes forming an undesired and potentially hazardous clot.

Soluble C3a is a small protein cleaved off from the complement factor 3 (C3) when this is bound and activated on a bacteria or a foreign body surface. C3a acts as a chemoattractant for polymorphonuclear (PMN) monocytes and also have anaphylatoxic properties signalling for the release of histamine from mast cells.

Material and Methods
Experimental Chambers

The experimental chamber is briefly constructed of two PMMA rings glued onto a PMMA microscopic slide, constructing two wells. After addition of whole blood, the material to be tested is placed as a lid over the two wells and held in position with a clip. The chamber is then mounted on a disc rotating in 37° C. water for 60 minutes at 22 rpm.

Blood

Blood was drawn from one healthy donor and collected in a 2× heparinized vial containing soluble heparin (Leo Pharma), to give a final concentration of 1.0 IU heparin/ml. The collected blood was then immediately transferred to the experimental chambers.

Platelet Counting

After incubation in the experimental chamber the blood was added EDTA (Fluka) to a final concentration of 4 mM. Platelets were then counted on a Coulter AcT Diff™ (Coulter Corporation) automated cell counter.

C3a Analysis

After platelet counting, the blood was centrifuged at 4600 g for 10 min at +4° C. and the supernatant (plasma) was saved and stored in −70° C. prior to measurements. Plasma was diluted 1/300 and analysed in a sandwich ELISA which employs the monoclonal 4SD17.3 (Uppsala university, Sweden) as capture antibody. Bound C3a was detected with biotinylated rabbit anti-human C3a (Dako), followed by HRP-conjugated streptavidin (Amersham Biosciences). Zymosan-activated serum, calibrated against a solution of purified C3a, served as a standard.

Results

The coated objects manufactured following the method outlined I example 2 on glass had a silver surface concentration of about 1.3 µg/cm$^2$.

| Sample | Amount of palladium (µg/cm$^2$) | Number of platelets (×10$^9$) | C3a (µg/ml) |
| --- | --- | --- | --- |
| Uncoated Glass | — | 29 | 681 |
| coating variation 1 | 0 | 170 | 337 |
| coating variation 2 | 0.01 | 190 | 287 |

Blood platelet count and C3a adsorption. The coatings on glass had a silver surface concentration of about 1.3 µg/cm$^2$.

| Sample | Amount of gold (µg/cm$^2$) | Number of platelets (×10$^9$) | C3a (µg/ml) |
| --- | --- | --- | --- |
| Uncoated Glass | — | 29 | 681 |
| Coating variation 3 | 0.01 | 166 | 376 |
| coating variation 4 | 0.01 | 141 | 271 |

Example 14

Measurement of Inflammatory Response

Material

NHSp-2 (Normal human serum pool from Immunologisk institutt, Rikshospitalet, Oslo, Norway), serum from healthy blood donors.

30 cm tubes made of PDMS (Polydimethylsiloxane) were coated according to the procedure outlined in example 2. 30 cm PVC tubes were used as control.

Setup: 7 types of tubes, untreated and PVC in triplicate (in total 21).

Method:
1) The serum was placed on ice.
2) A zero sample was removed. 750 µl was added directly to a tube with 15 µl EDTA 0.5M. The sample was kept on ice.
3) 750 µl serum was added to each tube.
4) The tubes were attached to a rotor (5 rpm) 37° C. and were incubated for 30 minutes.
5) The serum was removed with a pipette and added to a tube with 15 µl EDTA 0.5M. The samples were placed on ice and analysed with respect to TCC (the soluble terminal C5b-9 complement complex).

TCC was analyzed using a double antibody enzyme immunoassay based on the monoclonal aE11 antibody, highly specific for a neoepitope exposed on activated but not native C9, as catching antibody. The method was originally described in:
Mollnes T E, Lea T, Frøland SS, Harboe M. "Quantification of the terminal complement complex in human plasma by an enzyme-linked immunosorbent assay based on monoclonal antibodies against a neoantigen of the complex", *Scand J Immunol* 22:197-202. 1985.
and later modified in:
Mollnes T E, Redl H, Høgåsen K, Bengtsson A, Garred P, Speilberg L, Lea T, Oppermann M, Götze O, Schlag G. "Complement activation in septic baboons detected by neoepitope specific assays for C3b/iC3b/C3c, C5a and the terminal C5b-9 complement complex (TCC)", *Clin Exp Immunol* 91:295-300. 1993.

Results

The amount of Ag was 1 µg/cm$^2$.

| Sample No | Amount Pd (µg/cm$^2$) | TCC (pg/ml) | IL-8 (pg/ml) |
| --- | --- | --- | --- |
| 1 | 0.47 | 5.85 | 1582.13 |
| 2 | 0.70 | 5.16 | 1724.33 |
| 3 | 1.48 | 4.60 | 2136.79 |
| Uncoated PDMS tube | Uncoated | 3.88 | 728.33 |
| Uncoated PVC tube, control | Uncoated | 6.21 | 1750.23 |

The amount of Ag was 1 µg/cm$^2$.

| Sample No | Amount Au (µg/cm$^2$) | TCC (pg/ml) | IL-8 (pg/ml) |
| --- | --- | --- | --- |
| 4 | 0.14 | 5.24 | 1652.62 |
| 5 | 0.32 | 6.51 | 1264.40 |
| Uncoated PDMS tube | Uncoated | 3.88 | 728.33 |
| Uncoated PVC tube, control | Uncoated | 6.21 | 1750.23 |

Example 15

Cell Adhesion In Vitro and In Vivo

Primary normal human dermal fibroblasts (NHDF, Karocell Tissue Engineering AB, Stockholm, Sweden), passage 7, were used. The cells were cultured in tissue culture flasks in complete fibroblast medium containing DMEM+ GlutaMAX™-1 (Gibco, UK), 10% foetal bovine serum (FBS, Gibco, UK) and 1% Antibiotic-Antimycotic (Gibco, UK) at 37° C., 5% $CO_2$ and 95% humidity. Ten different substrates of silicon dioxide were coated following the method outlined in example 2 and were sterilely punched into discs with a diameter of 15 mm to fit in a 24-well plate. Discs were dipped in sterile PBS (Phospate buffered saline solution, Gibco, UK) and 1 ml of cell suspension (17000 cells/ml) was dispersed over the silicon dioxide disks and in empty PS-wells (polystyrene, Falcon, BD Biosciences, Belgium) and incubated for 24 h and 72 h in triplicates. Medium from all samples were collected, centrifuged at 400 g, 5 min and stored at −70° C. for ELISA (enzyme-linked immunosorbent assay) analyses of cell released factors. Two discs of each material were incubated with complete medium without cells to estimate background values.

Cell Amount

Cell amounts in association with the surfaces and surrounding medium were determined by a NucleoCounter®-system (ChemoMetec A/S, Denmark). Briefly, cells were treated with lysis buffer and stabilizing buffer (provided with the system). Lysed samples were loaded in a NucleoCassette™ precoated with fluorescent propidium iodide that stains the cell nuclei, and were then quantified in the NucleoCounter®.

Cell Viability

Cell viability was determined by measuring lactate dehydrogenase content (LDH) in medium, a marker of cell membrane injury, using a spectrophotometric evaluation of LDH mediated conversion of pyruvic acid to lactic acid (C-Laboratory, Sahlgrenska University Hospital, Göteborg, Sweden).

Cytokine Determination

The amount of TGF-β1 (Transforming Growth Factor beta 1) and type I collagen were detected by ELISA kits (Human TGF-β1, Quantikine®, R&D Systems, UK; Human collagen type1 ELISA KIT, Cosmo Bio Co., Japan) according to the manufacturer's instruction, in a SpectraVmax ELISA reader (Molecular Devices, UK).

In Vivo

Six different substrates of silicon dioxide (10 mm in diameter) were coated using the method outlined in example 2 and sterilized. Female Sprague-Dawley rats (200-250 g), fed on a standard pellet diet and water were anaesthetized with a mixture of 2,7% isofluran and air (Univentor 400 Anaesthesia Unit, Univentor, Malta) and 0.01 mg Temgesic was given as analgesic s.c. pre-operatively. Rats were shaved and cleaned with 5 mg/ml chlorohexidine in 70% ethanol and each rat received one of each implant type subcutaneously (s.c.) on the back. The wounds were closed with 2 sutures (Ethilon 5-0 FS-3, Ethicon®, Johnson & Johnson, Belgium). The implantation periods were 1 and 3 days to evaluate the early inflammatory process and 21 days for the examination of the fibrous capsule formation and the late inflammatory response (n=8 rats per time period). When the explantation was performed the animals were sacrificed by an overdose of pentobarbital (60 $gL^{-1}$) after short anaesthetics with a mixture of 2.7% isofluran and air. The implants and the surrounding exudates were retrieved. The exudate cells were obtained from the pockets by repeated aspiration of HBSS (Hank's balanced salt solution, Gibco, UK) and kept on ice. The exudates were centrifuged at 400 g, 5 min and supernatants were kept at −70° C. All implantation studies were approved by the Local Ethical Committee for Laboratory Animals.

Cell Amount and Cell Type

The concentration and type of cells in the exudates (cells/ml) were counted by light microscopy with Turk staining in a Bürker chamber and cell amount in centrifuged exudates and on implants were determined by NucleoCounter®-system.

Cell Viability

Cell viability was determined by Trypan Blue exclusion using light microscopy and by LDH evaluation (C-Laboratory, Sahlgrenska University Hospital, Göteborg, Sweden).

Cytokine Determination

The amount of TGF-β1 (Transforming Growth Factor beta 1) and MCP-1 (Monocyte Chemoattractant Protein-1) were detected by ELISA kits (Rat TGF-β1, Quantikine®, R&D Systems, UK; Amersham Monocyte Chemoattractant Protein-1 [(r)MCP-1], Rat, Biotrak ELISA System, GE Healthcare, UK) according to the manufacturer's instruction, in a SpectraVmax ELISA reader (Molecular Devices, UK).

Results from the In Vitro Study

The amount of metals on the test object was; Ag: 0.8-0.9 μg/cm$^2$ and Pd: 0.1 μg/cm$^2$.

| Surface concentration of Au (μg/cm$^2$) | Number of cells after 72 h |
|---|---|
| 0.05 | 5500 |
| 0.34 | 9400 |
| 0.43 | 16200 |

In the second experimental set the amount of metals on the test object was; Ag: 0.8-0.9 μg/cm$^2$ and Au: 0.05-0.09 μg/cm$^2$.

| Surface concentration of Pd (μg/cm$^2$) | Number of cells after 72 h |
|---|---|
| 0.1 | 5500 |
| 0.27 | 8600 |
| 0.69 | 9900 |

Results from the In Vivo Study

The Amount of Pd was varied on discs in vivo. The amount of Ag was about 1 μg/cm$^2$ for all samples. (PMN=polymorphonuclear)

| Amount of Pd (μg/cm$^2$) | % PMN cells in exudate, 1 day | % PMN cells in exudate, 3 days | % PMN cells in exudate, 21 days |
|---|---|---|---|
| Uncoated PDMS control | 33 | 2 | 1 |
| 0 | 17 | 2 | 1 |
| 0.07 | 32 | 2, 5 | Below 1 |
| 0.86 | 26 | 2 | Below 1 |

| Amount of Pd (μg/cm$^2$) | Total amount of MCP-1, 1 day (pg/ml) | Total amount of MCP-1, 3 days (pg/ml) | Total amount of MCP-1, 21 days (pg/ml) |
|---|---|---|---|
| Uncoated PDMS control | 4600 | 500 | 100 |
| 0 | 2050 | 700 | 350 |
| 0.07 | 4500 | 500 | 200 |
| 0.86 | 3300 | 600 | 200 |

| Amount of Pd (μg/cm$^2$) | Total amount of TGF-1, 1 day (pg/ml) | Total amount of TGF-1, 3 days (pg/ml) | Total amount of TGF-1, 21 days (pg/ml) |
|---|---|---|---|
| Uncoated PDMS control | 62 | 1 | 10 |
| 0 | 3 | 8 | 12 |
| 0.07 | 82 | 33 | 11 |
| 0.86 | 25 | 8 | 20 |

The Amount of Au was varied on discs in vivo. The amount of Ag was about 1 μg/cm$^2$ for all samples. (PMN=polymorphonuclear)

| Amount of Au (μg/cm$^2$) | % PMN cells in exudate, 1 day | % PMN cells in exudate, 3 days | % PMN cells in exudate, 21 days |
|---|---|---|---|
| Uncoated PDMS control | 33 | 2 | 1 |
| 0.01 | 32 | 2.5 | 1 |
| 0.43 | 18 | 5 | 1.5 |
| 0.64 | 20 | 4 | Below 1 |

| Amount of Au (μg/cm$^2$) | Total amount of MCP-1, 1 day (pg/ml) | Total amount of MCP-1, 3 days (pg/ml) | Total amount of MCP-1, 21 days (pg/ml) |
|---|---|---|---|
| Uncoated PDMS control | 4600 | 500 | 100 |
| 0.01 | 4500 | 500 | 200 |
| 0.43 | 3100 | 450 | 200 |
| 0.64 | 2800 | 500 | 150 |

| Amount of Au (μg/cm$^2$) | Total amount of TGF-1, 1 day (pg/ml) | Total amount of TGF-1, 3 days (pg/ml) | Total amount of TGF-1, 21 days (pg/ml) |
|---|---|---|---|
| Uncoated PDMS control | 62 | 1 | 10 |
| 0.01 | 82 | 33 | 11 |
| 0.43 | 6 | 5 | 20 |
| 0.64 | 28 | 8 | 9 |

The invention claimed is:

1. A substrate comprising an electron donating surface with metal particles on said surface, wherein each metal particle comprises palladium and at least one metal selected from the group consisting of gold, ruthenium, rhodium, osmium, iridium, and platinum, wherein the amount of said metal particles on said surface is from about 0.001 to about 8 μg/cm$^2$, wherein said metal particles have an average size of about 100 to about 10,000 Å, wherein said particles are distributed particles on said surface deposited on said surface from a colloidal suspension of the particles; and wherein the metal particles do not form a covering layer.

2. The substrate according to claim 1, wherein said electron donating surface is a layer of an electron donating material at an amount of about 0.05 to about 12 μg/cm$^2$.

3. The substrate according to claim 2, wherein said electron donating layer is a metal that is less noble than at least one of the metals in the group consisting of palladium, gold, ruthenium, rhodium, osmium, iridium, and platinum.

4. The substrate according to claim 2, wherein said electron donating layer is a metal selected from the group consisting of silver, copper and zinc.

5. The substrate according to claim 1, wherein said substrate is a polymeric substrate.

6. The substrate according to claim 1, wherein said substrate is selected from the group consisting of polymers comprising vinyl groups, silicone, polyvinylchloride, polypropylene, polyurethane, polyester, copolymerisates of ethylene vinyl acetate, polystyrene, polycarbonate, polyethylene, polyacrylate, polymethacrylate, acrylonitrile butadiene styrene, polyamide, and polyimide, or mixtures thereof.

7. The substrate according to claim 1, wherein said substrate is a metal.

8. The substrate according to claim 1, wherein said substrate is selected from the group consisting of stainless steel, titanium, cobalt, and chromium or mixtures thereof.

9. The substrate according to claim 1, wherein said substrate is selected from the group consisting of glass, minerals, zeolites, stone and ceramics.

10. The substrate according to claim 1, wherein said substrate is selected from the group consisting of paper, wood, woven fibres, fibres, cellulose fibres, leather, carbon, carbon fibres, graphite, polytetrafluoroethylene, and polyparaphenyleneterephthalamide.

11. The substrate according to claim 1, wherein said substrate has the shape of a particle.

12. The substrate according to claim 1 wherein the amount of the metal particles on the electron donating surface is from about 0.01 to about 4 μg/cm$^2$.

13. The substrate according to claim 2, wherein the weight ratio of palladium to the at least one metal selected from the group consisting of gold, ruthenium, rhodium, osmium, iridium, and platinum in said metal particles is from about 0.01:99.99 to about 99.99:0.01.

14. The substrate according to claim 2, wherein the weight ratio of palladium to the at least one metal selected from the group consisting of gold, ruthenium, rhodium, osmium, iridium, and platinum in said metal particles is from about 0.5:99.5 to about 99.8:0.2.

15. The substrate according to claim 2, wherein the weight ratio of palladium to the at least one metal selected from the group consisting of gold, ruthenium, rhodium, osmium, iridium, and platinum in said metal particles is from about 2:98 to about 95:5.

16. The substrate according to claim 1 wherein the at least one metal is gold.

17. The substrate according to claim 1, wherein said metal particles on the electron donating surface have average sizes of about 100 to about 600 Å.

18. An object comprising a substrate according to claim 1.

19. The object according to claim 18, wherein said object is a medical device.

20. The object according to claim 18, wherein said object is a disposable article.

21. The object according to claim 18, wherein said object is a dental article.

22. A method for modifying protein adsorption to an object, the method comprising applying the substrate of claim 1 to the object.

23. A method for modifying tissue ingrowth on an object, the method comprising applying the substrate of claim 1 to the object.

24. A method for modifying the complement activation caused by an object, the method comprising applying the substrate of claim 1 to the object.

25. A method for modifying the inflammatory response caused by an object, the method comprising applying the substrate of claim 1 to the object.

26. A method for modifying the blood clotting caused by an object, the method comprising applying the substrate of claim 1 to the object.

27. A method for modifying the friction coefficient of an object, the method comprising applying the substrate of claim 1 to the object.

28. A method for modifying the surface hardness of an object, the method comprising applying the substrate of claim 1 to the object.

29. A method for the manufacture of a substrate according to claim 1 comprising the steps:
   a. depositing metal particles from a colloidal suspension onto an object, wherein said object comprises the electron donating surface,
   b. rinsing said object, and
   c. drying said object.

30. A method according to claim 29 further comprising the step of depositing an electron donating material on said object to form the electron donating surface, before step a.

\* \* \* \* \*